United States Patent
Motoyama et al.

(10) Patent No.: US 6,217,954 B1
(45) Date of Patent: Apr. 17, 2001

(54) PHENYL TRIESTER COMPOUND AND ANTI-FERROELECTRIC LIQUID CRYSTAL COMPOSITION CONTAINING THE SAME

(75) Inventors: Yuki Motoyama; Takahiro Matsumoto; Masahiro Johno; Tomoyuki Yui, all of Katsushika-ku (JP)

(73) Assignee: Mitsubishi Gas Chemical Co Inc, Tokyo (JP)

(*) Notice: Subject to any disclaimer, the term of this patent is extended or adjusted under 35 U.S.C. 154(b) by 0 days.

(21) Appl. No.: 09/413,482

(22) Filed: Oct. 6, 1999

(30) Foreign Application Priority Data

Oct. 12, 1998 (JP) .................................. 10-289556

(51) Int. Cl.$^7$ ............................ C09K 19/12; C09K 19/20
(52) U.S. Cl. ................ 428/1.1; 252/299.64; 252/299.65; 252/299.66; 252/299.67
(58) Field of Search .................... 252/299.64, 299.65, 252/299.66, 299.67; 428/1.1

(56) References Cited

U.S. PATENT DOCUMENTS

| | | | |
|---|---|---|---|
| 5,938,973 | * | 8/1999 | Motoyama et al. ............ 252/299.65 |
| 5,976,409 | * | 11/1999 | Mineta et al. ................ 252/299.65 |

FOREIGN PATENT DOCUMENTS

| | | |
|---|---|---|
| 0829468 | 3/1998 | (EP) . |
| 0885876 | 12/1998 | (EP) . |
| 4198155 | 7/1992 | (JP) . |
| 9297311 | 11/1997 | (JP) . |
| 11-35941 | * 2/1999 | (JP) . |

OTHER PUBLICATIONS

Derwent Abstract 1998–596863.*
Japanese Journal of Applied Physics, vol. 27, pp. L729, 1988, "Tristable Switching in Surface Stabilized Ferroelectric Liquid Crystals with a Large Spontaneous Polarization".
Japanese Journal of Applied Physics, vol. 28, pp. L1261, 1989, "Novel Phases Exhibiting Tristable Switching".
Japanese Journal of Applied Physics, vol. 28, pp. L1265, 1989, "Antiferroelectric Chiral Smectic Phases Responsible for the Tristable Switching in MHPOBC".
Japanese Journal of Applied Physics, vol. 28, pp. L119, 1989, "Smectic Layer Switching by an Electric Field in Ferroelectric Liquid Crystal Cells".
Japanese Journal of Applied Physics, vol. 29, pp. L111, 1990, "Correspondence between Smectic Layer Switching and DC Hystersis of Apparent Tilt Angle in an Antiferroelectric Liquid Crystal Mixture".
Japanese Journal of Applied Physics, vol. 33, pp. L1620, 1994, "Smectic Layer Rotation in Antiferroelectric Liquid Crystal".
Chemical Abstracts, vol. 129, No. 21, 23 Nov. 1998 & JP 10 2521200 A (Abstract).
Chemical Abstracts, vol. 126. No. 24, 16 June 1997 (Abstract)
Booth, C.J., et al., "Achiral swallow–tailed materials with 'antiferroelectric–like' structure and their potential use in antiferroelectric mixtures" Liquid Crystals, GB, Taylor & Francis Ltd., vol. 20, No. 4, Apr. 1, 1996.

* cited by examiner

*Primary Examiner*—Shean C. Wu

(57) ABSTRACT

An anti-ferroelectric liquid crystal composition containing a phenyl triester compound of the formula (1),

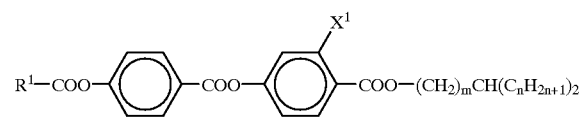

(1)

wherein $R^1$ is a linear alkyl group having 6 to 12 carbon atoms, m is an integer of 0 to 3, n is an integer of 1 to 3, and $X^1$ is a hydrogen atom or a fluorine atom, and an anti-ferroelectric liquid crystal compound of the formula (2),

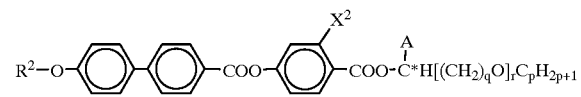

(2)

wherein $R^2$ is a linear alkyl group having 6 to 12 carbon atoms, $X^2$ is a hydrogen atom or a fluorine atom, A is —$CH_3$ or —$CF_3$, r is 0 or 1 and C* is an asymmetric carbon, provided that when A is —$CH_3$, r is 0 and p is an integer of 4 to 10, that when A is —$CF_3$ and when r is 0, p is an integer of 6 to 8, and further than when A is —$CF_3$ and when r is 1, q is an integer of 5 to 8 and p is 2 or 4. The phenyl triester compound and anti-ferroelectric liquid crystal compound composition is not only improved in response speed but also shows remarkably controlled layer rotation, and it can achieve a simple matrix liquid crystal display device which is free of a change in contrast and is highly reliable in use for a long period of time.

14 Claims, No Drawings

PHENYL TRIESTER COMPOUND AND ANTI-FERROELECTRIC LIQUID CRYSTAL COMPOSITION CONTAINING THE SAME

DETAILED DESCRIPTION OF THE INVENTION

1. Field of the Invention

The present invention relates to a novel phenyl triester compound and an anti-ferroelectric liquid crystal composition containing it and controlled layer rotation.

2. Prior Art

A liquid crystal display device has been so far used mainly for various small-sized display devices owing to its operability at low voltage, low power consumption and display performance with a thin screen. However, with recent increases in the application and use of liquid crystal display devices to/in the fields of information and office automation-related machines and equipment and the field of television sets, there are rapidly increasing demands for large-sized and high-performance liquid crystal display devices having larger display capacity and higher display quality than those of existing CRT display devices.

However, so long as a nematic liquid crystal available at present is used in a display device, even an active matrix liquid crystal display device (TFT) used in a liquid crystal television set finds it not easy to increase its size and decrease its production cost due to its complicated production process and a low yield. In a simple matrix STN liquid crystal display device (STN), the driving of a large-capacity display device is not necessarily easy and its response time is limited as well, so that video frame rate display is difficult to obtain. At present, therefore, it cannot at all be said that the nematic liquid crystal display device can satisfy demands toward the above high-performance large-sized liquid crystal display device.

As for display quality, further, both TFT and STN display devices using a nematic liquid crystal have a serious problem that the viewing angle is narrow. Although various improvement measures have been proposed, it is difficult to find out a drastic improvement measure so long as a nematic liquid crystal is used.

Under the circumstances, a liquid crystal display device for which a ferroelectric liquid crystal is used is attracting attention as a liquid crystal display device with a fast response speed and a wide viewing angel. A surface-stabilized ferroelectric liquid crystal (SSFLC) device disclosed by Clark and Lagerwall comes to notice in that it has a fast response speed and a wide viewing angle which have not been achieved in the past. Its switching characteristics have been studied in detail, and a number of ferroelectric liquid crystal compounds have been synthesized for optimizing various physical property constants.

When a ferroelectric liquid crystal is used as a liquid crystal display device, however, a special devising with regard to the alignment of the liquid crystal is required for achieving a contrast free of a problem in practical use, since it has an insufficient threshold characteristic and has a layer structure formed of a chevron structure. Further, since the alignment of its liquid crystal molecules is extremely difficult to control, it is not easy to attain the bistability, which is one of the most important characteristics of SSFLC, with good reproducibility. Further, there is another problem that when the alignment of the liquid crystal molecules is damaged by a mechanical shock, it is difficult to restore its alignment. It is therefore essentially required to overcome these problems in order to put the display device to practical use.

PROBLEMS TO BE SOLVED BY THE INVENTION

As described above, efforts including efforts to develop novel modes have been made in various ways for increasing the size of a liquid crystal display device and achieving a liquid crystal display with finer definition. Under the circumstances, development of display devices having switching mechanisms completely different from the prior devices is also under way simultaneously.

Switching among tristable states of a liquid crystal compound having an anti-ferroelectric phase (to be referred to as "anti-ferroelectric liquid crystal" hereinafter) is one of these new switching mechanisms (Japanese Journal of Applied Physics, Vol. 27, pp. L729, 1988).

The anti-ferroelectric liquid crystal device has three stable states, i.e., two uniform states (Ur, Ul) observed in a ferroelectric liquid crystal device and a third state. Chandani et al. report that the above third state is an anti-ferroelectric phase (Japanese Journal of Applied Physics, vol. 28, pp. L1261, 1989; ditto, pp. L1265). The above switching among three stable states is the first characteristic of an anti-ferroelectric liquid crystal device.

The second characteristic of the anti-ferroelectric liquid crystal device is that a sharp threshold value exists in respect to an applied voltage.

Further, the anti-ferroelectric liquid crystal device has a memory effect, and this is the third characteristic of the anti-ferroelectric liquid crystal device.

By utilizing the above excellent characteristic features, a liquid crystal display device having a fast response speed and a high contrast can be achieved.

The anti-ferroelectric liquid crystal device has another important characteristic that its layer structure easily performs switching when an electric field is applied (Japanese Journal of Applied Physics, Vol. 28, pp. L119, 1989; ditto, vol. 29, pp. L111, 1990).

On the basis of the above characteristics, there can be produced a liquid crystal display device having very few defect and the capability to self-restoring a molecule alignment, and a liquid crystal display device having an excellent contrast can be achieved.

However, when an anti-ferroelectric liquid crystal device is left in a driven state for a long period of time, there is sometimes observed a phenomenon that it shows a decrease in a display contrast.

One reason therefor is presumably that a smectic liquid crystal layer undergoes a layer rotation so that an extinction position shifts from an initial position (Japanese Journal of Phys. Vol. 33, pp. L1620, 1994).

The above layer rotation is a very important problem from the viewpoint of reliability in driving.

The expedient that is adopted against the layer rotation is presumably to increase the thickness of an alignment film to make it as large as possible, so that the alignment film is intensified in controlling force. However, the voltage which is generally effectively applied to a liquid crystal is expressed by the following equation.

$$V_{eff} = V_{ex} - P(d/\epsilon)$$

wherein Veff is a voltage actually applied to a liquid crystal, Vex is a driving voltage, P is a polarization of the liquid crystal, d is a thickness of an alignment film, and E is a dielectric constant of the alignment film.

As is clear from the above equation, the voltage actually applied to a liquid crystal decreases in proportion to a thickness of an alignment film, so that the voltage applied to the liquid crystal comes to be inadequate as the thickness of the alignment film increases, which results in a failure in obtaining a good display quality. There is therefore a limit to increasing the thickness of the alignment film for controlling a layer rotation.

Generally, further, the degree of the layer rotation increases with an increase in temperature. An attempt is made to maintain a panel temperature at a constant temperature for controlling the layer rotation to the extent that the display quality is not downgraded (Japanese Laid-open Patent Publication No. JP-A-9-297311). However, the above attempt requires addition of a temperature sensor, a temperature controller and a cooling system to a panel, and it undesirably results in an increase in the cost of the panel as a whole. It is therefore the most advantageous to improve liquid crystal materials for solution.

Means to Solve the Problems

The present inventors have therefore made diligent studies for developing a compound which functions to control the layer rotation when contained into an anti-ferroelectric liquid crystal compound. As a result, the present invention has been arrived at.

According to the present invention, therefore, there is provided a novel phenyl triester compound of the formula (1),

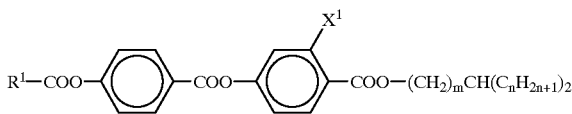
(1)

wherein $R^1$ is a linear alkyl group having 6 to 12 carbon atoms, m is an integer of 0 to 3, n is an integer of 1 to 3, and $X^1$ is a hydrogen atom or a fluorine atom.

According to the present invention, further, there is provided an anti-ferroelectric liquid crystal composition comprising substantially at least one of phenyl triester compounds of the formula (1),

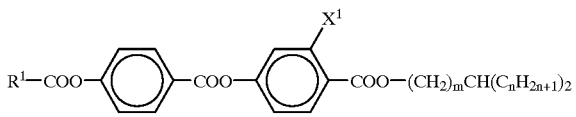
(1)

wherein $R^1$ is a linear alkyl group having 6 to 12 carbon atoms, m is an integer of 0 to 3, n is an integer of 1 to 3, and $X^1$ is a hydrogen atom or a fluorine atom, and at least one of anti-ferroelectric liquid crystal compounds of the formula (2),

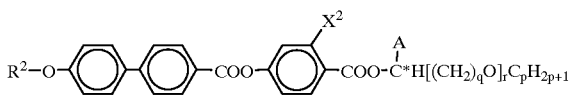
(2)

wherein $R^2$ is a linear alkyl group having 6 to 12 carbon atoms, $X^2$ is a hydrogen atom or a fluorine atom, is —$CH_3$ or —$CF_3$, r is 0 or 1 and C* is an asymmetric carbon, provided that when A is —$CH_3$, r is 0 and p is an integer of 4 to 10, that when A is —$CF_3$ and when r is 0, p is an integer of 6 to 8, and further that when A is —$CF_3$ and when r is 1, q is an integer of 5 to 8 and p is 2 or 4.

The phenyl triester compound of the present invention and the anti-ferroelectric liquid crystal composition containing the same, provided by the present invention, will be explained further in detail hereinafter.

The phenyl triester compound of the present invention has the above formula (1). In the formula (1), $R^1$ is a linear alkyl group having 6 to 12 carbon atoms, and $R^1$ is preferably a linear alkyl group having 8 to 12 carbon atoms, more preferably a linear alkyl group having 9 carbon atoms. m is an integer of 0 to 3, preferably 0, 1 or 2. n is an integer of 1 to 3, preferably 1 or 2. Particularly preferred is a compound of the formula (1) in which m is 2 and n is 1. $X^1$ is a hydrogen atom or a fluorine atom, and $X^1$ is preferably a fluorine atom.

When mixed with an anti-ferroelectric liquid crystal compound, the phenyl triester compound of the present invention exhibits the activity of controlling the layer rotation of the anti-ferroelectric liquid crystal compound. Therefore, the phenyl triester compound of the present invention can be advantageously used as a component for a liquid crystal composition valuable as a liquid crystal material by mixing it with an anti-ferroelectric liquid crystal compound having a difficulty in controlling the layer rotation thereof and a consequent problem in the practical use thereof.

The phenyl triester compound of the present invention gives an anti-ferroelectric liquid crystal composition having a layer rotation controlled and having excellent characteristics when mixed with an anti-ferroelectric liquid crystal compound of the above formula (2).

In the above formula (2), $R^2$ is a linear alkyl group having 6 to 12 carbon atoms, preferably a linear alkyl group having 8 to 12 carbon atoms. $X^2$ is a hydrogen atom or a fluorine atom, and $X^2$ is preferably a fluorine atom. A is —$CH_3$ or —$CF_3$, r is 0 or 1, and C* is an asymmetric carbon. However, when A is —$CH_3$, r is 0 and p is an integer of 4 to 10. When A is —$CF_3$ and when r is 0, p is an integer of 6 to 8. When A is —$CF_3$ and when r is 1, q is an integer of 5 to 8, and p is 2 or 4.

Of compounds of the above formula (2), (i) a compound of the formula (2) in which A is —$CF_3$, r is 1, q is an integer of 5 to 8 and p is 2 or 4 and (ii) a compound of the formula (2) in which A is —$CH_3$, r is 0 and p is an integer of 6 to 8 are excellent as an anti-ferroelectric liquid crystal compound. Compounds of the formula (2) may be used alone or in combination. An anti-ferroelectric liquid crystal composition comprising a combination of the compounds specified in the above (i) and (ii) is excellent since it is well-balanced among various characteristics.

In the anti-ferroelectric liquid crystal composition of the present invention, desirably, the amount ratio (mol %) of the compound of the formula (1):compound of the formula (2) is 70-20:30-80, preferably 60-30:40-70. Preferably in practical use, further, the anti-ferroelectric liquid crystal composition of the present invention has a smectic A phase on a temperature side higher than the temperature range of its anti-ferroelectric phase, the upper limit temperature of the temperature range of the anti-ferroelectric phase is 40° C. or upper, and the lower limit temperature of the temperature range of the anti-ferroelectric phase is 0° C. or lower.

Further, preferably, the anti-ferroelectric liquid crystal composition of the present invention shows a layer rotation of 1° or less at 50° C. when an asymmetrical rectangular wave is applied at a voltage of 40 V, at a pulse width of 100 ms at a temperature of 50° C. for 10 minutes, and particularly preferably, it undergoes substantially no layer rotation at 40° C. when an asymmetrical rectangular wave is applied at a voltage of 40 V, at a pulse width of 100 ms at a temperature of 40° C. for 10 minutes.

Further, when the anti-ferroelectric liquid crystal composition of the present invention is used in a simple matrix liquid crystal display device formed by filling it between a pair of electrode substrates where scanning electrodes and signal electrodes are arranged in a matrix form, the anti-ferroelectric liquid crystal composition of the present invention can achieve a highly reliable liquid crystal display device which is free from a decrease in contrast when driven for a long period of time.

The phenyl triester compound of the formula (1), provided by the present invention, can be produced, by the following method, for example, when it has the formula (1) in which $R^1=C_9H_{19}$, m=2, n=1 and $X^1=F$.

(a) AcO—Ph(2F)—COOH+$SOCl_2$→AcO—Ph(2F)—COCl (b) (a)+$(CH_3)_2CHCH_2CH_2OH$→AcO—Ph(2F)—COO—$CH_2CH_2CH(CH_3)_2$ (c) (b)+$(CH_3NH_2)$→HO—Ph(2F)—COO—$CH_2CH_2CH(CH_3)_2$ (d) $C_9H_{19}$—COCl+HO—Ph—COOH→$C_9H_{19}$—COO—Ph—COOH (e) (d)+$SOCl_2$→$C_9H_{19}$—COO—Ph—COCl (f) (c)+(e)→$C_9H_{19}$—COO—Ph—COO—Ph(3F)—COO—$CH_2CH_2CH(CH_3)_2$

In the above formulae, —Ph— is a 1,4-phenylene group, —Ph(2F)— and —Ph(3F)— is a 1,4-phenylene group in which fluorine is substituted on the 3-position from an OH residue bonding position, and Ac is an acetyl group.

The above production method will be briefly explained below.

(a) shows the chlorination of 4-acetoxybenzoic acid with thionyl chloride.

(b) shows a reaction between acid chloride (a) and 3-methylbutanol.

(c) shows the deacetylation of an ester (b).

(d) shows a reaction between decanoyl chloride and p-hydroxybenzoic acid.

(e) shows the chlorination of a carboxylic acid compound (d) with thionyl chloride.

(f) shows the production of an end product by a reaction between a phenol (c) and an acid chloride (e).

Further, the anti-ferroelectric liquid crystal compound of the formula (2) used in the present invention can be easily produced by a method disclosed by the present inventors (Japanese Laid-open Patent Publication No. JP-A-4-198155). For example, a compound of the formula (2) in which A=—$CF_3$, r=1, q=5 and p=2 is produced by the following method.

(1) AcO—Ph(X)—COOH+$SOCl_2$→AcO—Ph(X)—COCl (2) (1)+HOC*H($CF_3$)$(CH_2)_5OC_2H_5$→AcO—Ph(X)—COOC*H($CF_3$)$(CH_2)_5OC_2H_5$ (3) (2)+Ph—$CH_2NH_2$→HO—Ph(X)—COOC*H($CF_3$)$(CH_2)_5OC_2H_5$ (4) $R^2O$—Ph—Ph—COOH+$SOCl_2$→$R^2O$—Ph—Ph—COCl (5) (3)+(4)→anti-ferroelectric liquid crystal compound In the above formulae, —Ph— is a 1,4-phenylene group, —Ph(X)— is a 1,4-phenylene group in which fluorine may be substituted, Ph— is a phenyl group, and C* is an asymmetric carbon.

The above production method will be briefly explained below.

(1) shows the chlorination of a fluorine-substituted or non-substituted p-acetoxybenzoic acid with thionyl chloride.

(2) shows esterification by a reaction between a chlorination compound (1) and an alcohol.

(3) shows the deacetylation of an ester (2).

(4) shows the chlorination of alkyloxybiphenylcarboxylic acid.

(5) shows the formation of a liquid crystal compound by a reaction between a phenol (3) and an acid chloride (4).

EXAMPLES

The present invention will be explained more in detail with reference to Examples and Comparative Examples hereinafter, while the present invention shall not be limited thereto.

Example 1

(formula (1): $R^1=C_9H_{19}$, m=2, n=1, $X^1=F$ (E1))
Preparation of 3-fluoro-4-(3-methylbutyloxycarbonyl)phenyl-4'-decanoyloxybenzoate (1) Preparation of 4-decanoyloxybenzoic Acid 12.2 Grams (0.1 mol) of 4-hydroxybenzoic acid was dissolved in 140 ml (milliliters) of dichloromethane. Further, 16 ml of triethylamine, 20.1 g (0.11 mol) of n-decanoic acid chloride and 0.97 g (0.0079 mol) of dimethylaminopyridine were consecutively added, and the mixture was stirred at room temperature for one day.

To the mixture was added 50 ml of 10% hydrochloric acid, and the mixture was extracted with 100 ml of ether three times. An organic layer was washed with 100 ml of a sodium chloride aqueous solution three times, and then dried over anhydrous sodium sulfate.

The solvent was distilled off, and the residue was washed with 400 ml of hexane to give 23.9 g (yield 82%) of an end product.

(2) Preparation of 4-acetoxy-2-fluoro-1-(3-methylbutyloxycarbonyl)benzene

To 10.8 g (0.06 mol) of 4-acetoxy-2-fluorobenzoic acid was added 60 ml of thionyl chloride, and the mixture was allowed to react under reflux for 7 hours.

Then, excessive thionyl chloride was distilled off, and then 10 ml of pyridine and 4.1 g (0.0402 mol) of 3-methylbutanol were dropwise added. After the dropwise addition, the mixture was stirred at room temperature for one day and then diluted with 200 ml of ether. An organic layer was washed with diluted hydrochloric acid, a 1N sodium hydroxide aqueous solution and then water in this order, and dried over magnesium sulfate.

The solvent was distilled off, and a crude end product was purified by silica gel column chromatography using hexane/ethyl acetate, to give 10.2 g (yield 90%) of an end product.

(3) Preparation of 4-hydroxy-2-fluoro- 1-(3-methylbutyloxycarbonyl)benzene 10.2 Grams (0.0361 mol) of the compound obtained in the above (2) was dissolved in 250 ml of ethanol, and 7.7 g (0.0772 mol) of benzylamine was dropwise added. Further, the mixture was stirred at room temperature for one day, diluted with 300 ml of ether, washed with diluted hydrochloric acid and then water in this order, and dried over magnesium sulfate.

The solvent was distilled off, and the residue was purified by silica gel column chromatography for isolation, to give 8.4 g (0.0356 mol; yield 98%) of an end product.

(4) Preparation of 3-fluoro-4-(3-methylbutyloxycarbonyl)phenyl-4'-n-decanoyloxybenzoate To 3.1 mmol of the compound obtained in the above (2) was added 15 ml of thionyl chloride, and the mixture was refluxed under heat for 5 hours. Excessive thionyl chloride was distilled off, then, 2 ml of pyridine and 2.12 mmol of the compound obtained in the above (3) were added, and the mixture was allowed to react at room temperature for 10 hours.

After completion of the reaction, the reaction mixture was diluted with 300 ml of ether, and washed with diluted hydrochloric acid, a 1N sodium carbonate aqueous solution and then water in this order, and an organic layer was dried over magnesium sulfate.

Then, the solvent was distilled off, and the residue was subjected to silica gel column chromatography for isolation, to give 9.2 g (1.84 mmol; yield 85%) of an end product.

Example 2

(formula (1): $R^1=C_{11}H_{23}$, m=1, n=2, $X^1$=F (E2))
Preparation of 3-fluoro-4-(3-ethylbutyloxycarbonyl)phenyl-4'-dodecanoyloxybenzoate An end product was prepared in the same manner as in Example 1 except that the n-decanoic acid chloride in (1) of Example 1 was replaced with undecanoic acid chloride.

Example 3

(formula (1): $R^1=C_9H_{19}$, m=0, n=2, $X^1$=F (E3))
Preparation of 3-fluoro-4-(1-ethylpropyloxycarbonyl)phenyl-4'-decanoyloxybenzoate An end product was prepared in the same manner as in Example 1 except that the 3-methylbutanol in Example 1 was replaced with 1-ethylpropanol.

Table 1 shows $^1$H-NMR data of the end products obtained in Examples 1, 2 and 3, and the chemical structures thereof are shown below Table 1.

TABLE 1

| | Chemical Shift (ppm) Hydrogen atom No. | | | | | | | |
|---|---|---|---|---|---|---|---|---|
| | 1H | 2H | 3H | 4H | 5H | 6H | 7H | 8H |
| Example 1 (E1) | 2.6 | 7.3 | 8.2 | 7.1 | — | 7.1 | 8.0 | 4.4 |
| Example 2 (E2) | 2.6 | 7.3 | 8.2 | 7.1 | — | 7.1 | 8.0 | 4.3 |
| Example 3 (E3) | 2.6 | 7.3 | 8.2 | 7.1 | — | 7.1 | 8.0 | 4.3 |

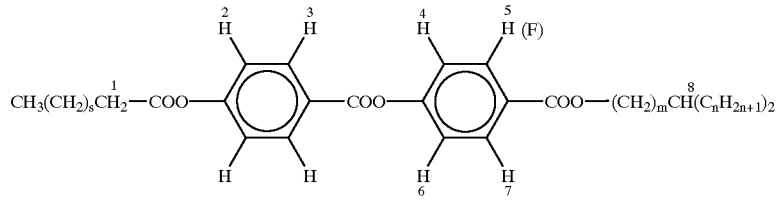

Example 4

The phenyl triester compound (E1) obtained in Example 1 was added to a mixture of the following anti-ferroelectric liquid crystal compounds (2A and 2B) corresponding to the compound of the formula (2) in the present invention, to obtain an anti-ferroelectric liquid crystal composition having each content as shown below.

| E1: $C_9H_{19}$—COO—Ph—COO—Ph(3F)—COO—$(CH_2)_2CH(CH_3)_2$ | 40 mol % |
|---|---|
| 2A: $C_9H_{19}$—O—Ph—Ph—COO—Ph(3F)—COO—C*H($CF_3$)$(CH_2)_5OC_2H_5$ | 37.5 mol % |
| 2B: $C_9H_{19}$—O—Ph—Ph—COO—Ph(3F)—COO—C*H($CH_3$)$C_5H_{11}$ | 22.5 mol % |

In the above formulae, —Ph— is a 1,4-phenylene group, —Ph(3F)— is a 1,4-phenylene group in which fluorine is substituted on the 3-position from an OH residue side, and C* is an asymmetric carbon atom.

Example 5

A liquid crystal composition was prepared in the same manner as in Example 4 except that E1 obtained in Example 1 was replaced with E2 obtained in Example 2.

Example 6

A liquid crystal composition was prepared in the same manner as in Example 4 except that E1 obtained in Example 1 was replaced with E3 obtained in Example 3.

Comparative Example 1

An anti-ferroelectric liquid crystal composition was prepared in the same manner as in Example 1 except that the phenyl triester compound (E1) obtained in Example 1 was not used and that the anti-ferroelectric liquid crystal compounds (2A and 2B) amount ratio was changed to 2A/2B= 60/40 (molar ratio).

The anti-ferroelectric liquid crystal compositions obtained in Examples 4 to 6 and Comparative Example 1 were measured for a phase sequence, a response speed and a layer rotation, and Table 2 shows the results.

The response speed and the layer rotation were measured as follows.

A liquid crystal cell (cell gap 2 μm) having ITO electrodes coated with a rubbed polyimide thin film (30 nm) was filled with the above composition in an isotropic state. Then, the cell was gradually cooled at a rate of 1.0° C./minute to align the liquid crystal. The cell was set between the crossed polarizers such that the layer direction of the liquid crystal was in parallel with an analyzer or a polarizer.

The minimum of light transmittance was determined to be 0%, and the maximum of light transmittance was determined to be 100%. The response time I was determined to be a length of time required for a change in the light transmittance from 10% to 90% when a voltage of 35 V and 10 Hz was applied at 30° C., and the response time II was determined to be a length of time required for a change in the light transmittance from 90% to 10%.

Further, the layer rotation was determined by applying a wave-shaped voltage having cycles each of which consisted of (1)+40 V, 100 ms→(2) changing from +40 V to −40 V for 100 ms→(3) −40 V, 100 ms→(4) immediately changing to +40 V, for 10 minutes, and then observing the liquid crystal through a microscope for a shift from an extinction position before applying voltage as a reference (0°) after the above voltage was applied.

TABLE 2

| | | Response time*1 | | Layer rotation*2 | |
|---|---|---|---|---|---|
| | Phase sequence | I | II | 40° C. | 50° C. |
| Ex. 4 | Cr(<−20)SCA*(74)SA(96)I | 22 | 4800 | 0 | 0.6 |
| Ex. 5 | Cr(<−20)SCA*(70)SA(94)I | 40 | 6500 | 0 | 2.1 |
| Ex. 6 | Cr(<−20)SCA*(73)SA(97)I | 20 | 6700 | 0 | 1.0 |
| CEx. 1 | Cr(<−10)SCA*(58)SC*(101)SA(111)I | 106 | 15000 | 0.7 | 4.5 |

Ex. = Example, CEx. = Comparative Example
*1Unit, μ second, measurement temperature 30° C.
*2Unit, ° (an angle of degrees)

In the phase sequence, parenthesized values show phase transfer temperatures (° C.), Cr is a crystal phase, SCA* is an anti-ferroelectric phase, SC* is a ferroelectric phase, SA is a smectic A phase, and I is an isotropic phase.

EFFECT OF THE INVENTION

The present invention provides a novel phenyl triester compound. An anti-ferroelectric liquid crystal composition comprising the above phenyl triester compound is not only improved in response speed but also shows remarkably controlled layer rotation, and it can achieve a simple matrix liquid crystal display device which is free of a change in contrast and is highly reliable in use for a long period of time.

What is claimed is:

1. An anti-ferroelectric liquid crystal composition comprising substantially at least one of phenyl triester compounds of the formula (1),

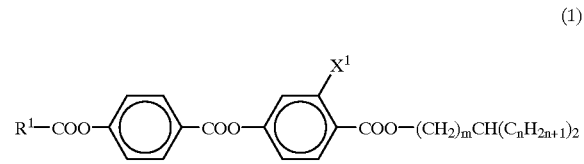

(1)

wherein $R^1$ is a linear alkyl group having 6 to 12 carbon atoms, m is an integer of 0 to 3, n is an integer of 1 to 3, and $X^1$ is a hydrogen atom or a fluorine atom,
and at least one of anti-ferroelectric liquid crystal compounds of the formula (2),

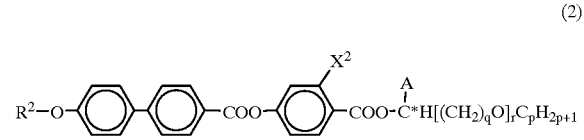

(2)

wherein $R^2$ is a linear alkyl group having 6 to 12 carbon atoms, $X^2$ is a hydrogen atom or a fluorine atom, A is —$CH_3$ or —$CF_3$, r is 0 or 1 and C* is an asymmetric carbon, provided that when A is —$CH_3$, r is 0 and p is an integer of 4 to 10, that when A is —$CF_3$ and when r is 0, p is an integer of 6 to 8, and further that when A is —$CF_3$ and when r is 1, q is an integer of 5 to 8 and p is 2 or 4.

2. The anti-ferroelectric liquid crystal composition of claim 1, wherein $R^1$ in the formula (1) is a linear alkyl group having 8 to 12 carbon atoms.

3. The anti-ferroelectric liquid crystal composition of claim 1, wherein m in the formula (1) is 0, 1 or 2.

4. The anti-ferroelectric liquid crystal composition of claim 1, wherein n in the formula (1) is 1 or 2.

5. The anti-ferroelectric liquid crystal composition of claim 1, wherein $X^1$ in the formula (1) is a fluorine atom.

6. The anti-ferroelectric liquid crystal composition of claim 1, wherein, in the formula (2), A is —$CF_3$, r is 1, q is an integer of 5 to 8 and p is 2 or 4.

7. The anti-ferroelectric liquid crystal composition of claim 1, wherein, in the formula (2), A is —$CH_3$, r is 0 and p is an integer of 6 to 8.

8. The anti-ferroelectric liquid crystal composition of claim 1, which contains at least one of the phenyl triester compounds of the formula (1) and at least one of the anti-ferroelectric liquid crystal compounds of the formula (2) in a phenyl triester compound:anti-ferroelectric liquid crystal compound molar ratio of 60-30:40-70.

9. The anti-ferroelectric liquid crystal composition of claim 1, wherein the composition has a smectic A phase on a temperature side higher than a temperature range of anti-ferroelectric phase thereof, the upper limit temperature of a temperature range of anti-ferroelectric phase thereof is 40° C. or upper, and the lower limit temperature of a temperature range of anti-ferroelectric phase thereof is 0° C. or lower.

10. The anti-ferroelectric liquid crystal composition of claim 1, wherein the composition shows a layer rotation of 1° or less at 50° C. when an asymmetrical rectangular wave is applied at a voltage of 40 V, at a pulse width of 100 ms at a temperature of 50° C. for 10 minutes.

11. The anti-ferroelectric liquid crystal composition of claim 1, wherein the composition undergoes substantially no layer rotation at 40° C. when an asymmetrical rectangular wave is applied at a voltage of 40 V, at a pulse width of 100 ms at a temperature of 40° C. for 10 minutes.

12. An anti-ferroelectric liquid crystal display device in which the anti-ferroelectric liquid crystal composition of claim 1 is filled between a pair of electrode substrates.

13. A method for preparing an anti-ferroelectric liquid crystal composition which comprises adding a phenyl tri-ester compound-of the formula (1),

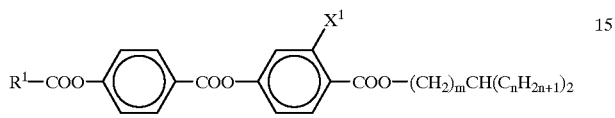

(1)

wherein $R^1$ is a linear alkyl group having 6 to 12 carbon atoms, m is an integer of 0 to 3, n is an integer of 1 to 3, and $X^1$ is a hydrogen atom or a fluorine atom, to at least one anti-ferroelectric compound.

14. The method of claim 13 wherein the at least one anti-ferroelectric compound has the formula (2),

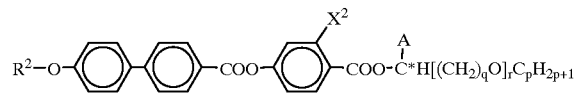

(2)

wherein $R^2$ is a linear alkyl group having 6 to 12 carbon atoms, $X^2$ is a hydrogen atom or a fluorine atom, A is —$CH_3$ or —$CF_3$, r is 0 or 1 and C* is an asymmetric carbon, provided that when A is —$CH_3$, r is 0 and p is an integer of 4 to 10, that when A is —$CF_3$ and when r is 0, p is an integer of 6 to 8, and further that when A is —$CF_3$ and when r is 1, q is an integer of 5 to 8 and p is 2 or 4.

* * * * *